United States Patent
Kato et al.

[11] Patent Number: 5,997,707
[45] Date of Patent: Dec. 7, 1999

[54] OXIDE SENSOR

[75] Inventors: Nobuhide Kato, Ama-gun; Kunihiko Nakagaki, Nagoya, both of Japan

[73] Assignee: NGK Insulators, Ltd., Japan

[21] Appl. No.: 08/824,557

[22] Filed: Mar. 25, 1997

[30] Foreign Application Priority Data

Mar. 28, 1996 [JP] Japan ................................ 8-074716
Mar. 10, 1997 [JP] Japan ................................ 9-055232

[51] Int. Cl.$^6$ .................................................. G01N 27/41
[52] U.S. Cl. ..................... 204/425; 204/426; 204/427; 205/781; 205/784; 205/784.5
[58] Field of Search .................... 204/421–429; 205/783.5, 784, 784.5, 785, 780.5, 781

[56] References Cited

U.S. PATENT DOCUMENTS

| | | | |
|---|---|---|---|
| 4,264,425 | 4/1981 | Kimura et al. | 204/425 |
| 4,770,760 | 9/1988 | Noda et al. | 204/425 |
| 4,824,549 | 4/1989 | Hamada et al. | 204/410 |
| 4,927,517 | 5/1990 | Mizutani et al. | 204/425 |
| 4,950,380 | 8/1990 | Kurosawa et al. | 204/406 |
| 5,098,549 | 3/1992 | Friese et al. | 204/426 |
| 5,145,566 | 9/1992 | Logothetis et al. | 204/424 |
| 5,304,294 | 4/1994 | Wang et al. | 204/426 |
| 5,397,442 | 3/1995 | Wachsman | 205/781 |
| 5,476,001 | 12/1995 | Hoetzel et al. | 73/23.31 |
| 5,672,811 | 9/1997 | Kato et al. | 204/427 |

FOREIGN PATENT DOCUMENTS

| | | |
|---|---|---|
| 0678740 | 10/1995 | European Pat. Off. . |
| 0769693 | 4/1997 | European Pat. Off. . |
| 0791828 | 8/1997 | European Pat. Off. . |
| 0831322 | 3/1998 | European Pat. Off. . |
| 95/30146 | 11/1995 | WIPO . |
| WO 95/30146 | 11/1995 | WIPO . |

*Primary Examiner*—T. Tung
*Attorney, Agent, or Firm*—Parkhurst & Wendel, L.L.P.

[57] ABSTRACT

Disclosed is an oxide sensor in which $O_2$ contained in a measurement gas introduced into a first chamber through a first diffusion rate-determining section is removed by the aid of a pumping voltage applied between pumping electrodes, and then the measurement gas is introduced into a second chamber through a second diffusion rate-determining section to remove excessive $O_2$ by the aid of auxiliary pumping electrodes. A detecting electrode is arranged to satisfy $d \geq t$ provided that d represents a distance from an end of the auxiliary pumping electrodes on the side of the second diffusion rate-determining section to an end of the detecting electrode on the side of the second diffusion rate-determining section, and t represents a height of the second chamber. A predetermined pumping voltage is applied to the detecting electrode to decompose oxides contained in the measurement gas by the aid of the detecting electrode or a catalyst. The amount of oxygen produced by the decomposition is measured to determine the concentration of the oxides. Accordingly, the amount of the oxides in the measurement gas can be measured extremely highly accurately without being affected by water and carbon dioxide contained in the measurement gas.

12 Claims, 12 Drawing Sheets

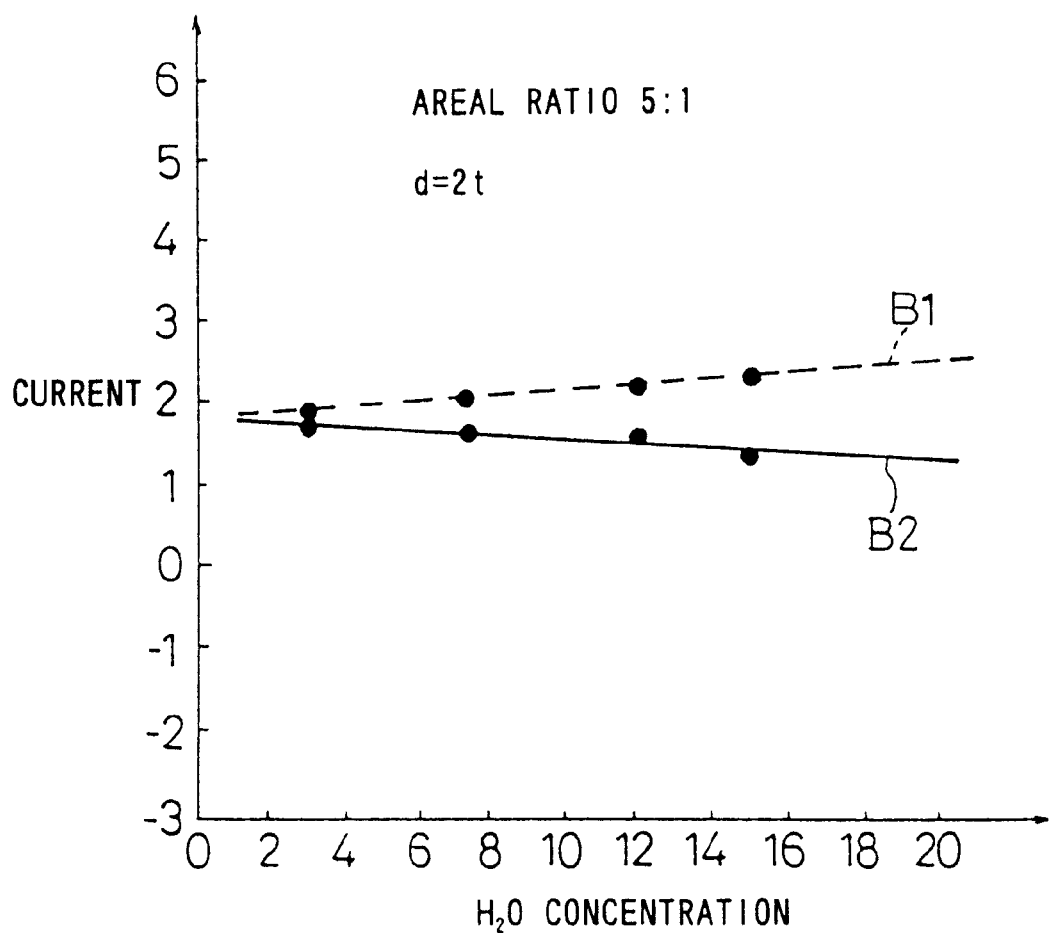

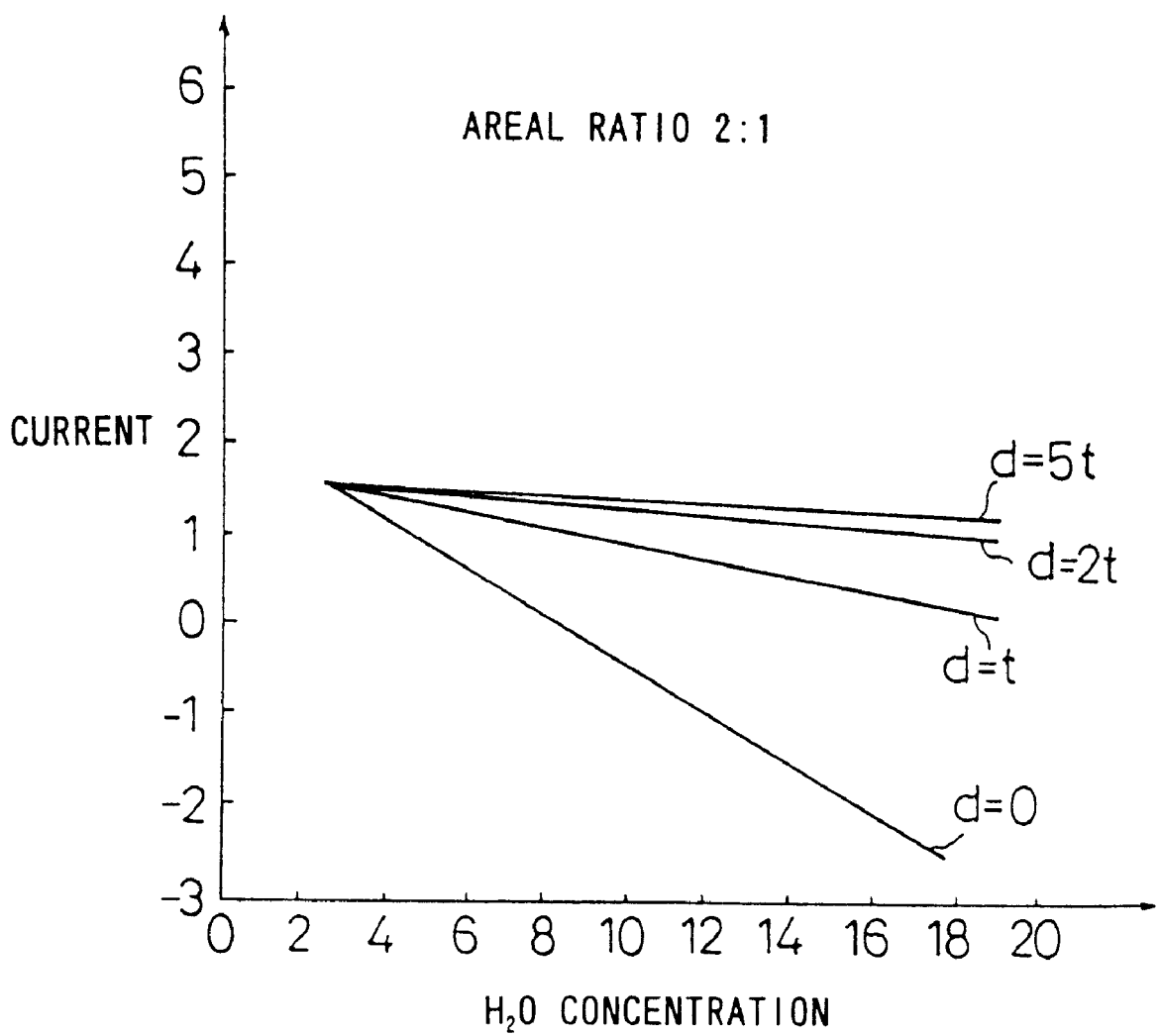

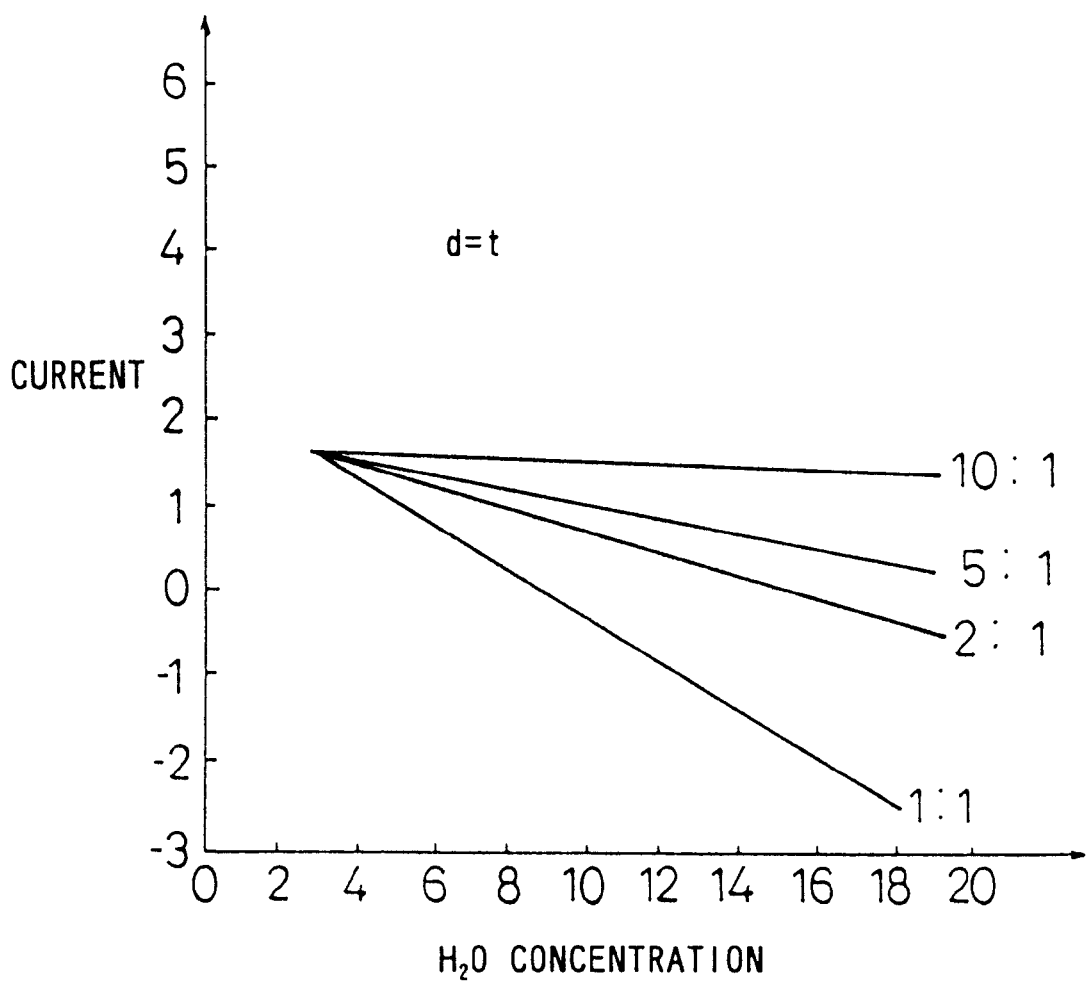

OXIDE SENSOR

BACKGROUND OF THE INVENTION

1. Field of the Invention

The present invention relates to an oxide sensor for measuring oxides such as NO, $NO_2$, $SO_2$, $CO_2$, and $H_2O$ contained in, for example, atmospheric air and exhaust gas discharged from vehicles or automobiles. In particular, the present invention relates to an oxide sensor for measuring NO and $NO_2$.

2. Description of the Related Art

Exhaust gas, which is discharged, for example, from vehicles or automobiles such as gasoline-fueled automobiles and diesel powered automobiles, contains nitrogen oxides (NOx) such as nitrogen monoxide (NO) and nitrogen dioxide ($NO_2$), as well as carbon monoxide (CO), carbon dioxide ($CO_2$), water ($H_2O$), hydrocarbon (CnHm), hydrogen ($H_2$), oxygen ($O_2$) and so on. In such exhaust gas, about 80% of the entire NOx is occupied by NO, and about 95% of the entire NOx is occupied by NO and $NO_2$.

The three way catalyst, which is used to clean HC, CO, and NOx contained in the exhaust gas, exhibits its maximum cleaning efficiency in the vicinity of the theoretical air fuel ratio (A/F=14.6). If A/F is controlled to be not less than 16, the amount of produced NOx is decreased. However, the cleaning efficiency of the catalyst is lowered, and consequently the amount of discharged NOx is apt to increase.

Recently, in order to effectively utilize fossil fuel and avoid global warming, the market demand increases, for example, in that the discharge amount of $CO_2$ should be suppressed. In order to respond to such a demand, it becomes more necessary to improve the fuel efficiency. In response to such a demand, for example, the lean burn engine and the catalyst for cleaning NOx are being researched. Especially, the need for a NOx sensor increases.

A conventional NOx analyzer has been hitherto known as an instrument for detecting NOx. The conventional NOx analyzer is operated to measure a characteristic inherent in NOx, based on the use of chemical luminous analysis. However, the conventional NOx analyzer is inconvenient in that the instrument itself is extremely large and expensive. The conventional NOx analyzer requires frequent maintenance because optical parts are used to detect NOx. Further, when the conventional NOx analyzer is used, any sampling operation should be performed for measurement of NOx, and hence it is impossible to directly insert a detecting element itself into a fluid. Therefore, the conventional NOx analyzer is not suitable for analyzing transient phenomena such as those occur in the exhaust gas discharged from an automobile, in which the condition frequently varies.

In order to dissolve the inconveniences as described above, there has been already suggested a sensor for measuring a desired gas component in exhaust gas by using a substrate comprising an oxygen ion-conductive solid electrolyte.

FIG. 14 shows a system of a gas analyzer disclosed in International Publication WO 95/30146. This apparatus comprises a first chamber 4 into which a measurement gas containing NO is introduced through a narrow hole 2, and a second chamber 8 into which the measurement gas is introduced from the first chamber 4 through a narrow hole 6. Wall surfaces for constructing the first and second chambers 4, 8 are composed of partition walls 10a, 10b made of zirconia ($ZrO_2$) capable of transmitting oxygen ion. A pair of measuring electrodes 12a, 12b and a pair of measuring electrodes 14a, 14b for measuring the partial pressure of oxygen in the respective chambers are arranged on portions of one $ZrO_2$ partition wall 10a corresponding to the first and second chambers 4, 8 respectively. A set of pumping electrodes 16a, 16b and a set of pumping electrodes 18a, 18b for pumping out $O_2$ in the respective chambers to the outside of the chambers are arranged on the other $ZrO_2$ partition wall 10b.

The gas analyzer thus constructed functions as follows. Namely, the partial pressure of oxygen contained in the measurement gas introduced into the first chamber 4 through the narrow hole 2 is detected by a voltmeter 20 as an electric potential difference generated between the measuring electrodes 12a, 12b. A voltage of 100 to 200 mV is applied between the pumping electrodes 16a, 16b by the aid of a power source 22 so that the electric potential difference is adjusted to have a predetermined value. Accordingly, $O_2$ in the first chamber 4 is pumped out to the outside of the apparatus. The amount of pumped out oxygen can be measured by using an ammeter 24.

The measurement gas, from which almost all $O_2$ has been removed, is introduced into the second chamber 8 through the narrow hole 6. In the second chamber 8, an electric potential difference generated between the measuring electrodes 14a, 14b is detected by a voltmeter 26. Thus the partial pressure of oxygen in the second chamber 8 is measured. On the other hand, NO contained in the measurement gas introduced into the second chamber 8 is decomposed as follows by the aid of a voltage applied between the pumping electrodes 18a, 18b by means of a power source 28:

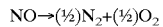

$O_2$ produced by the decomposition is pumped out to the outside of the second chamber 8 by the aid of the pumping electrodes 18a, 18b. A value of an electric current generated during this process is detected by an ammeter 30. Thus the concentration of NO contained in the measurement gas is measured.

However, in the case of the gas analyzer constructed as described above, if the concentration of oxygen contained in the measurement gas is high, $O_2$ in the first chamber 4 cannot be sufficiently pumped out to the outside of the chamber 4 by the aid of the pumping electrodes 16a, 16b. As a result, unprocessed excessive $O_2$ enters the second chamber 8 together with NO. Therefore, an error due to the unprocessed excessive $O_2$ is included in the current value obtained by decomposition of NO.

Therefore, in order to remove excessive $O_2$ introduced into the second chamber 8, a system may be conceived, in which an auxiliary pumping electrode is arranged in the second chamber 8, and the excessive $O_2$ is removed to detect a partial pressure of oxygen based on only NO so that the concentration of NO is detected highly accurately.

However, in the case of the system constructed as described above, an inconvenience arises in that when a large amount of, for example, $H_2O$ and $CO_2$ is contained in the measurement gas, the measured value of NO is lowered in a degree corresponding to the amount of the contained gas described above.

Namely, parts of $H_2O$ and $CO_2$ introduced into the first chamber 4 are decomposed on the pumping electrode 16b in accordance with the following reaction formulas:

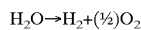

$$CO_2 \rightarrow CO + (\tfrac{1}{2})O_2$$

$O_2$ produced by the decomposition is pumped out to the outside by the aid of the pumping electrodes 16a, 16b, while $H_2$ and CO as inflammable gases are introduced into the second chamber 8. In such a situation, if the $H_2$ and CO introduced into the second chamber 8 arrive at the pumping electrode 18b without being oxidized, the $H_2$ and CO react with $O_2$ produced by decomposition of NO by the aid of the pumping electrode 18b. If such reactions occur, the amount of $O_2$ pumped out to the outside of the second chamber 8 by the pumping electrode 18a, 18b is decreased. Therefore, the current flowing through the ammeter 30 is also decreased. It is noted that the amounts of $H_2$ and CO which enter the second chamber 8 vary depending on the concentration of $H_2O$ and $CO_2$ in the measurement gas. Therefore, the amount of oxygen decreased upon being pumped out to the outside of the second chamber 8 is not constant, and hence it is difficult to measure the concentration of NO highly accurately.

SUMMARY OF THE INVENTION

The present invention has been made in order to overcome the inconvenience described above, an object of which is to provide an oxide sensor which makes it possible to measure the amount of oxides contained in a measurement gas with an extremely high degree of accuracy without being affected, for example, by water and carbon dioxide contained in the measurement gas.

In order to achieve the object described above, the present invention provides an oxide sensor comprising a main pumping means including inner and outer pumping electrodes arranged on inner and outer surfaces of a substrate composed of an oxygen ion-conductive solid electrolyte, for performing a pumping process for oxygen contained in a measurement gas introduced from external space, on the basis of a control voltage applied between the inner and outer pumping electrodes; an electric signal-generating conversion means including inner and outer detecting electrodes arranged on inner and outer surfaces of a substrate composed of an oxygen ion-conductive solid electrolyte, for decomposing oxides contained in the measurement gas after being subjected to the pumping process performed by the main pumping means, by the aid of a catalytic action and/or electrolysis to provide, by conversion, an electric signal corresponding to an amount of oxygen produced by the decomposition; and an auxiliary pumping means including inner and outer auxiliary pumping electrodes arranged on the inner and outer surfaces of the substrates composed of the oxygen ion-conductive solid electrolyte, for performing a pumping process for oxygen contained in the measurement gas after being subjected to the pumping process performed by the main pumping means, on the basis of an auxiliary pumping voltage applied between the inner and outer auxiliary pumping electrodes; wherein the inner detecting electrode is arranged at a position separated from the inner auxiliary pumping electrodes, the position being located on a downstream side of a flow of the measurement gas, and the oxides contained in the measurement gas are measured on the basis of the electric signal supplied from the electric signal-generating conversion means.

According to the present invention, at first, the oxygen in the measurement gas introduced from the external space is subjected to the pumping process performed by the main pumping means, and the oxygen is adjusted to have a predetermined concentration. The measurement gas, in which the oxygen concentration has been adjusted by the main pumping means, is introduced into the electric signal-generating conversion means in the next step. The electric signal-generating conversion means serves to decompose the oxides contained in the measurement gas after being subjected to the pumping process performed by the main pumping means, by the aid of the catalytic action and/or electrolysis, and provide, by conversion, the electric signal corresponding to the amount of oxygen produced by the decomposition. After that, the oxides contained in the measurement gas are measured on the basis of the electric signal supplied from the electric signal-generating conversion means.

The oxide sensor may comprise a measuring pumping means and a current-detecting means to serve as the electric signal-generating conversion means. In this preferred embodiment, the measurement gas, in which the oxygen concentration has been adjusted by the main pumping means, is introduced into the measuring pumping means.

In the measuring pumping means, the oxides contained in the measurement gas after being subjected to the pumping process performed by the main pumping means are decomposed by the aid of the catalytic action and/or electrolysis. The oxygen produced by the decomposition is subjected to a pumping process performed by the measuring pumping means on the basis of a measuring voltage applied between inner and outer detecting electrodes. A pumping current is generated in the measuring pumping means, corresponding to an amount of oxygen subjected to the pumping process performed by the measuring pumping means. The generated pumping current is detected by the current-detecting means. Thus the oxides are measured, corresponding to the amount of oxygen.

In another preferred embodiment, the oxide sensor of the present invention may comprise a concentration-detecting means and a voltage-detecting means to serve as the electric signal-generating conversion means. In this embodiment, the measurement gas, in which the concentration of oxygen has been adjusted by the main pumping means, is introduced into the concentration-detecting means in the next step. In the concentration-detecting means, the oxides contained in the measurement gas after being subjected to the pumping process performed by the main pumping means are decomposed by the aid of the catalytic action. The concentration-detecting means generates an electromotive force of an oxygen concentration cell, corresponding to a difference between an amount of oxygen produced by the decomposition and an amount of oxygen contained in a gas existing on a side of an outer detecting electrode. The generated electromotive force is detected by the voltage-detecting means. Thus the oxides are measured, corresponding to the amount of oxygen.

In the oxide sensor according to the present invention, for example, parts of $H_2O$ and $CO_2$ contained in the measurement gas introduced from the external space are decomposed by the inner pumping electrode, and inflammable gases are produced, during the measurement of the oxides. The inflammable gases are introduced into the process space processed by the electric signal-generating conversion means, together with the oxides as the measurement-objective predetermined gas components.

The inner auxiliary pumping electrodes for constructing the auxiliary pumping means are arranged in the process space processed by the electric signal-generating conversion means. The inner detecting electrode for constructing the electric signal-generating conversion means is also arranged therein at the position separated from the inner auxiliary pumping electrodes, the position being located on the downstream side of the flow of the measurement gas. According to the present invention, the amount of oxygen contained in the measurement gas introduced into the process space processed by the electric signal-generating conversion means is adjusted to be constant by pumping out the oxygen contained in the measurement gas by the aid of the auxiliary pumping means, or by pumping the oxygen contained in the external space into the process space.

Accordingly, the oxides are decomposed without being affected by the inflammable gases, by the aid of the inner detecting electrode arranged at the position separated from the inner auxiliary pumping electrodes, the position being located on the downstream side of the flow of the measurement gas, or the oxides are decomposed by the aid of an oxide-decomposing catalyst arranged in the process space processed by the electric signal-generating conversion means.

When the electric signal-generating conversion means includes the measuring pumping means and the current-detecting means, the oxygen produced by the decomposition of the oxides is pumped out to the outside of the process space through the substrate by the aid of the measuring pumping means, without being affected by the inflammable gases. A pumping current is generated thereby, which is detected by the current-detecting means. Thus the amount of the oxides is measured with a high degree of accuracy.

On the other hand, when the electric signal-generating conversion means includes the concentration-detecting means and the voltage-detecting means, the oxygen produced by the decomposition of the oxides serves to generate an electromotive force of the oxygen concentration cell, corresponding to a difference between the amount of oxygen produced by the decomposition of the oxides and the amount of oxygen contained in the gas existing on the side of the outer detecting electrode, without being affected by the inflammable gases. The electromotive force is detected by the voltage-detecting means. Thus the amount of the oxides is measured with a high degree of accuracy.

Especially, it is preferable for the oxide sensor according to the present invention that the inner detecting electrode is arranged at a position separated by not less than t from an upstream end of the inner auxiliary pumping electrodes provided that t represents a height of the process space for the measurement gas after being subjected to the pumping process performed by the main pumping means, i.e., a height of the process space processed by the measuring pumping means or the concentration-detecting means.

The inner detecting electrode has an area which is not more than ½, more preferably not more than ⅕ of an area of the inner auxiliary pumping electrodes. Thus the oxides can be measured more accurately.

In a preferred embodiment, the inner detecting electrode has its surface covered with a protective layer composed of a porous material. Thus the influence exerted by the inflammable gases can be further decreased. It is preferable that the protective layer is composed of a porous material comprising a major component of alumina or zirconia.

Preferably, the inner auxiliary pumping electrodes are arranged on at least upper and lower surfaces, and optionally on side surfaces of the process space for the measurement gas after being subjected to the pumping process performed by the main pumping means. Thus it is possible to more appropriately eliminate the influence exerted by the inflammable gases.

It is preferable that the inner auxiliary pumping electrodes are composed of an inactive material having a low catalytic activity on the oxides. In this embodiment, it is possible to suppress decomposition of NO which may be caused by the inner auxiliary pumping electrodes. Accordingly, the error in measurement is preferably decreased. The inactive material includes a cermet comprising a ceramic and Au or a noble metal added with Au.

A plurality of process spaces (referred to as "second chambers" for convenience) processed by the measuring pumping means or the concentration-detecting means, which are linked to the process space (referred to as "first chamber" for convenience) processed by the main pumping means, may be arranged in series or in parallel to the first chamber. Thus a plurality of oxides of different types can be measured by using one sensor in each of the second chambers by individually setting the pumping voltage applied between the electrodes of the measuring pumping means, corresponding to each of the measurement-objective oxides, or by individually setting a decomposing catalyst arranged in the measuring pumping means or the concentration-detecting means, corresponding to each of the measurement-objective oxides.

The inner pumping electrode for constructing the main pumping means may be composed of an inactive material having a low catalytic activity on the oxides. In this embodiment, the oxide-decomposing reaction on the inner pumping electrodes is suppressed more appropriately. Thus the oxides can be measured with a higher degree of accuracy by the aid of the measuring pumping means or the concentration-detecting means.

In a preferred embodiment, the control voltage supplied to the main pumping means is set so that the electromotive force of the oxygen concentration cell is not more than 350 mV. Thus it is possible to supply the measurement gas adjusted to have a desired oxygen concentration, to the process space processed by the measuring pumping means or the concentration detecting means.

Especially, nitrogen oxides such as NO and $NO_2$ can be measured highly accurately by using the oxide sensor according to the present invention.

It is preferable that each of the substrates for constructing each of the process spaces is heated to a predetermined temperature by using a heating means in order to give desired characteristics of oxygen ion conductivity. In this embodiment, it is preferable that the electrodes arranged in the process space processed by the measuring pumping means or the concentration-detecting means are arranged on the substrate located on a side of the heating means.

A means for giving a predetermined diffusion resistance to the measurement gas (referred to as "first diffusion rate-determining section" for convenience) may be arranged between the external space and the process space processed by the main pumping means. Further, a means for giving a predetermined diffusion resistance to the measurement gas (referred to as "second diffusion rate-determining section" for convenience) may be arranged between the process space processed by the main pumping means and the process space processed by the measuring pumping means or the concentration-detecting means. In this embodiment, it is desirable that the diffusion resistance of the second diffusion rate-determining section is set to be larger than the diffusion resistance of the first diffusion rate-determining section.

It is preferable to use an Rh cermet as the oxide-decomposing catalyst arranged in the process space processed by the measuring pumping means or the concentration-detecting means. The oxide-decomposing catalyst may be provided as the electrode. Alternatively, the oxide-decomposing catalyst may be provided as a catalyst layer separately from the electrode.

In the oxide sensor according to the present invention, the outer detecting electrode is arranged at a position exposed to a space into which the reference gas is introduced. Thus the oxygen produced by the decomposition of the oxides can be compared with the oxygen contained in the reference gas, making it possible to detect the oxides more accurately.

Especially, it is preferable that the outer detecting electrode is combined into a common unit with the outer auxiliary pumping electrode. In this embodiment, a common electrode, which serves as the outer detecting electrode of the measuring pumping means or the concentration-detecting means, and the outer auxiliary pumping electrode, is exposed to the reference gas-introducing space. The common electrode can be defined as a reference electrode for the respective detecting processes performed by the measuring pumping means and the concentration-detecting means. In accordance with this definition, the inner detecting electrode of the measuring pumping means and the concentration-detecting means can be defined as a detecting electrode, and the inner auxiliary pumping electrode of the auxiliary pumping means can be defined as an auxiliary electrode.

The oxide sensor according to the present invention may further comprise an oxygen partial pressure-detecting means including a measuring electrode arranged in the process space processed by the main pumping means and a reference electrode arranged in the reference gas-introducing space, for detecting an electromotive force of an oxygen concentration cell, generated between the measuring electrode and the reference electrode to detect a partial pressure of oxygen in the process space, wherein the control voltage for the main pumping means is controlled so that the partial pressure of oxygen detected by the oxygen partial pressure-detecting means has a predetermined value. Thus the measurement gas in the process space is allowed to have a predetermined oxygen concentration.

In this embodiment, the reference electrode is preferably arranged on a wall surface of an atmospheric air-introducing section associated with the oxide sensor, and the reference electrode is preferably combined into a common unit with the outer auxiliary pumping electrode and the outer detecting electrode.

The inner detecting electrode for constructing the measuring pumping means or the concentration-detecting means may also serves as an oxide-decomposing catalyst.

The above and other objects, features and advantages of the present invention will become more apparent from the following description when taken in conjunction with the accompanying drawings in which a preferred embodiment of the present invention is shown by way of illustrative example.

DESCRIPTION OF THE DRAWINGS

FIG. 8 shows characteristics representing the relationship among the value of current flowing through auxiliary pumping electrodes, the value of current flowing through a detecting electrode, and the concentration of $H_2O$, concerning Example 2.

FIG. 9 shows characteristics representing the relationship between the value of current flowing through a detecting electrode and the concentration of $H_2O$, obtained by fixing the areal ratio of auxiliary pumping electrodes to the detecting electrode, and changing the distance of the detecting electrode from a second diffusion rate-determining section, concerning Example 3.

FIG. 10 shows characteristics representing the relationship between the value of current flowing through a detecting electrode and the concentration of $H_2O$, obtained by fixing the distance of the detecting electrode from a second diffusion rate-determining section, and changing the areal ratio of auxiliary pumping electrodes to the detecting electrode, concerning Example 4.

DESCRIPTION OF THE PREFERRED EMBODIMENTS

Several illustrative embodiments, in which the oxide sensor according to the present invention is applied to oxide sensors for measuring oxides such as NO, $NO_2$, $SO_2$, $CO_2$, and $H_2O$ contained in, for example, atmospheric air and exhaust gas discharged from vehicles or automobiles, will be explained below with reference to FIGS. 1 to 13.

Figure 1:
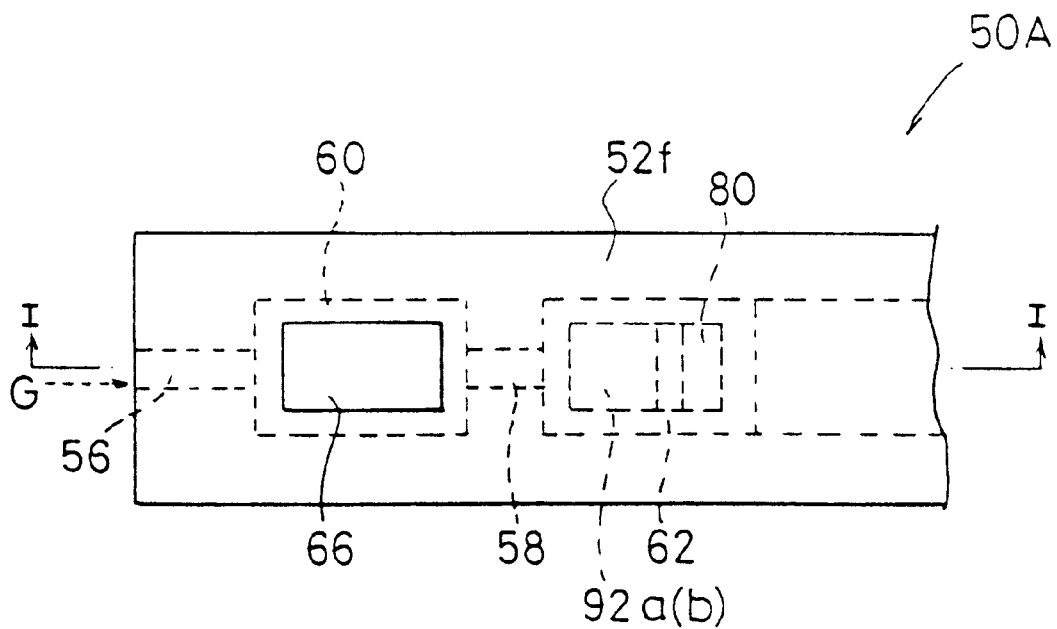
FIG. 1 shows a plan view illustrating an oxide sensor according to a first embodiment.
Figure 2:
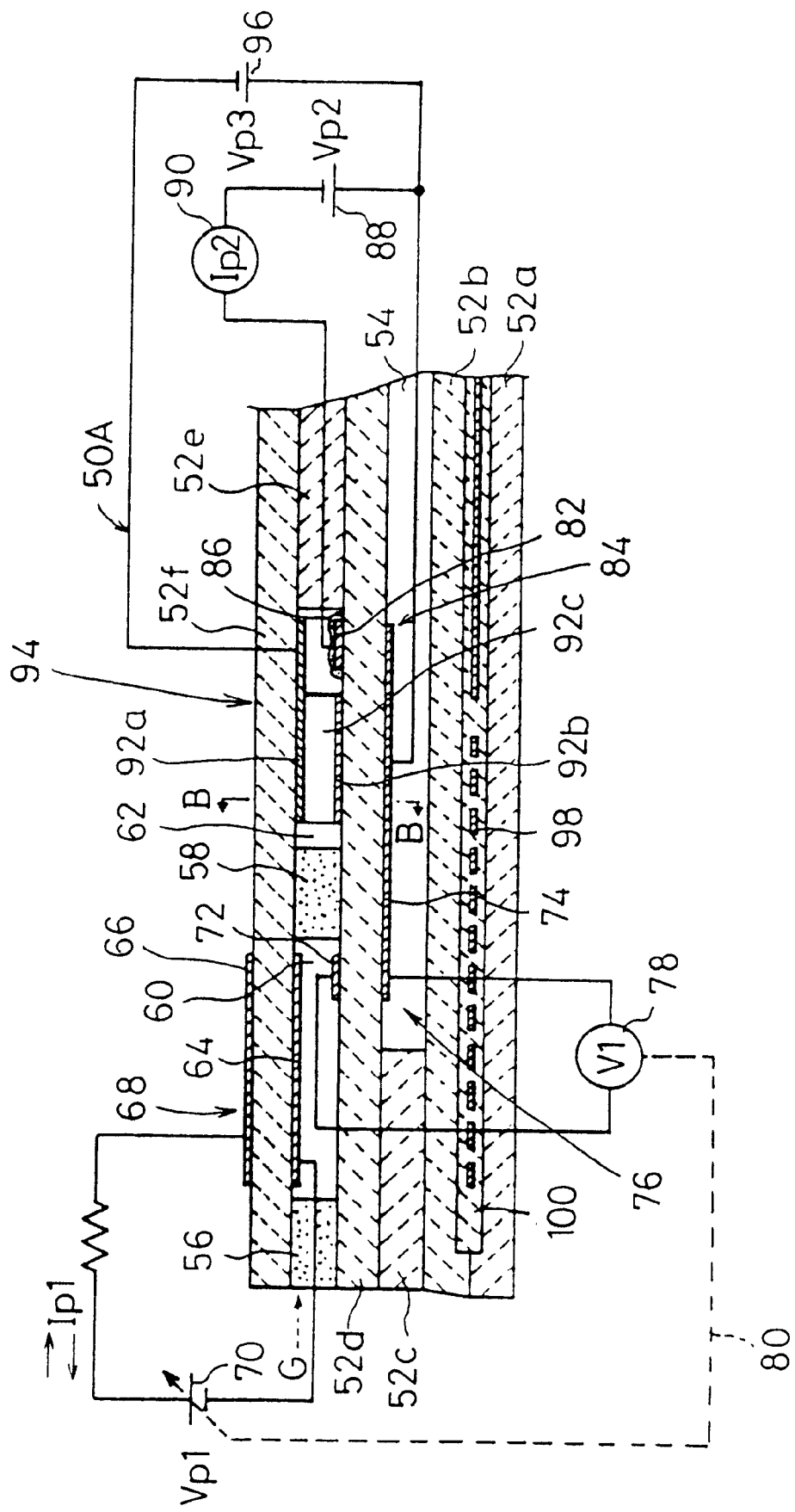
FIG. 2 shows a cross-sectional view taken along a line A—A in FIG. 1.

At first, as shown in FIGS. 1 and 2, an oxide sensor 50A according to a first embodiment has a lengthy plate-shaped configuration making up a substrate as a whole, wherein the overall substrate is comprised of six stacked solid electrolyte layers 52a to 52f composed of ceramics based on the use of oxygen ion-conductive solid electrolytes such as $ZrO_2$. First and second layers from the bottom are designated as first and second substrate layers 52a, 52b respectively. Third and fifth layers from the bottom are designated as first and second spacer layers 52c, 52e respectively. Fourth and sixth layers from the bottom are designated as first and second solid electrolyte layers 52d, 52f respectively.

Specifically, the first spacer layer 52c is stacked on the second substrate layer 52b. The first solid electrolyte layer 52d, the second spacer layer 52e, and the second solid electrolyte layer 52f are successively stacked on the first spacer layer 52c.

A space (reference gas-introducing space 54), into which a reference gas such as atmospheric air to be used as a reference for measuring oxides is introduced, is formed between the second substrate layer 52b and the first solid electrolyte layer 52d, the space being comparted by a lower surface of the first solid electrolyte layer 52d, an upper surface of the second substrate layer 52b, and a side surface of the first spacer layer 52c.

The second spacer layer 52e is interposed between the first and second solid electrolyte layers 52d, 52f. First and second diffusion rate-determining sections 56, 58 are also interposed between the first and second solid electrolyte layers 52d, 52f.

A first chamber 60 for adjusting the partial pressure of oxygen in a measurement gas G is formed and comparted by a lower surface of the second solid electrolyte layer 52f, side surfaces of the first and second diffusion rate-determining sections 56, 58, and an upper surface of the first solid electrolyte layer 52d. A second chamber 62 for finely adjusting the partial pressure of oxygen in the measurement gas G and measuring oxides, for example, nitrogen oxides (NOx) in the measurement gas G is formed and comparted by a lower surface of the second solid electrolyte layer 52f, a side surface of the second diffusion rate-determining section 58, a side surface of the second spacer layer 52e, and an upper surface of the first solid electrolyte layer 52d.

The external space communicates with the first chamber 60 through the first diffusion-rate determining section 56, and the first chamber 60 communicates with the second chamber 62 through the second diffusion rate-determining section 58.

The first and second diffusion-rate determining sections 56, 58 give predetermined diffusion resistances to the measurement gas G to be introduced into the first and second chambers 60, 62 respectively. Each of the first and second diffusion-rate determining sections 56, 58 can be formed as a passage composed of, for example, a porous material, or a small hole having a predetermined cross-sectional area so that the measurement gas G may be introduced. When the distance between the first and second solid electrolyte layers 52d, 52f is narrow, the first and second chamber 60, 62 may form a continuous flat space.

Especially, the second diffusion-rate determining section 58 is arranged and filled with a porous material comprising, for example, $ZrO_2$. The diffusion resistance of the second diffusion-rate determining section 58 is made larger than the diffusion resistance of the first diffusion-rate determining section 56.

An atmosphere in the first chamber 60 is introduced into the second chamber 62 under the predetermined diffusion resistance through the second diffusion rate-determining section 58. Therefore, the oxide sensor 50A has the following directional characteristic. Namely, the measurement gas G existing in the external space is introduced into the oxide sensor 50A in a direction of the first diffusion rate-determining section 56→the first chamber 60→the second diffusion rate-determining section 58→the second chamber 62. This direction can be defined as "downstream direction" for the measurement gas G.

An inner pumping electrode 64, which is composed of a porous cermet electrode having a flat and substantially rectangular shape, is formed on an entire surface portion for forming the first chamber 60, of the lower surface of the second solid electrolyte layer 52f. An outer pumping electrode 66 is formed on a portion corresponding to the inner pumping electrode 64, of the upper surface of the second solid electrolyte layer 52f. An electrochemical pumping cell, i.e., a main pumping cell 68 is constructed by the inner pumping electrode 64, the outer pumping electrode 66, and the second solid electrolyte layer 52f interposed between the both electrodes 64, 66.

A desired control voltage (pumping voltage) Vp1 is applied between the inner pumping electrode 64 and the outer pumping electrode 66 of the main pumping cell 68 by the aid of an external variable power source 70 to allow a pumping current Ip1 to flow in a positive or negative direction between the outer pumping electrode 66 and the inner pumping electrode 64. Thus the oxygen in the atmosphere in the first chamber 60 can be pumped out to the external space, or the oxygen in the external space can be pumped into the first chamber 60.

A measuring electrode 72, which is composed of a porous cermet electrode having a flat and substantially rectangular shape, is formed on a portion adjacent to the second diffusion rate-determining section 58, of the upper surface of the first solid electrolyte layer 52d for forming the first chamber 60. A reference electrode 74 is formed on a portion exposed to the reference gas-introducing space 54, of the lower surface of the first solid electrolyte layer 52d. An electrochemical sensor cell, i.e., a controlling oxygen partial pressure-detecting cell 76 is constructed by the measuring electrode 72, the reference electrode 74, and the first solid electrolyte layer 52d.

An electromotive force is generated between the measuring electrode 72 and the reference electrode 74 of the controlling oxygen partial pressure-detecting cell 76 on the basis of a difference in oxygen concentration between the atmosphere in the first chamber 60 and the reference gas (atmospheric air) in the reference gas-introducing space 54. The partial pressure of oxygen in the atmosphere in the first chamber 60 can be detected by measuring the generated electromotive force by the aid of a voltmeter 78.

Namely, the voltage V1, which is generated between the reference electrode 74 and the measuring electrode 72, is an electromotive force of the oxygen concentration cell, generated on the basis of a difference between a partial pressure of oxygen in the reference gas introduced into the reference gas-introducing space 54 and a partial pressure of oxygen in the measurement gas G in the first chamber 60. The voltage V1 has the following relationship known as the Nernst's equation.

$$V1 = RT//4F \cdot \ln(P1(O_2)/PO(O_2))$$

R: gas constant;
T: absolute temperature;
F: Faraday constant;
P1($O_2$)): partial pressure of oxygen in the first chamber 60;
PO($O_2$)): partial pressure of oxygen in the reference gas.

Therefore, the partial pressure of oxygen in the first chamber 60 can be detected by measuring the voltage V1 generated on the basis of the Nernst's equation, by the aid of the voltmeter 78.

The detected value of the partial pressure of oxygen is used to control the pumping voltage of the variable power source 70 by the aid of a feedback control system 80. Specifically, the pumping operation performed by the main pumping cell 68 is controlled so that the partial pressure of oxygen in the first chamber 60 has a predetermined value which is sufficiently low to control the partial pressure of oxygen in the second chamber 62 in the next step.

The inner pumping electrode 64 and the outer pumping electrode 66 are composed of an inactive material having a low catalytic activity on NOx, for example, NO in the measurement gas G introduced into the first chamber 60. Specifically, the inner pumping electrode 64 and the outer pumping electrode 66 can be composed of a porous cermet electrode. In this embodiment, they are formed of a metal such as Pt and a ceramic such as $ZrO_2$. Especially, it is necessary, for the inner pumping electrode 64 and the measuring electrode 72 arranged in the first chamber 60 contacting with the measurement gas G, to use a material having a weak reducing ability or no reducing ability with respect to the NOx components in the measurement gas. It is preferable that the inner pumping electrode 64 and the measuring electrode 72 are composed of, for example, a compound having the perovskite structure such as $La_3CuO_4$, a cermet comprising a ceramic and a metal having a low catalytic activity such as Au, or a cermet comprising a ceramic, a metal of the Pt group, and a metal having a low catalytic activity such as Au. Further, when an alloy comprising Au and a metal of the Pt group is used as an electrode material, it is preferable to add Au in an amount of 0.03 to 35 volt of the entire metal components.

The oxide sensor 50A according to the first embodiment includes a detecting electrode 82 composed of a porous cermet electrode having a flat and substantially rectangular shape. The detecting electrode 82 is formed on a portion separated from the second diffusion rate-determining section 58, of the upper surface of the first solid electrolyte layer 52d for forming the second chamber 62. An electrochemical pumping cell, i.e., a measuring pumping cell 84 is constructed by the detecting electrode 82 (also referred to as the first detecting electrode), the reference electrode 74 (also referred to as the second detecting electrode), and the first solid electrolyte layer 52d. Further, a protective layer 86, which is composed of, for example, a porous $Al_2O_3$ layer or a porous $ZrO_2$ layer, is formed to cover the detecting electrode 82 of the measuring pumping cell 84.

The detecting electrode 82 can be constructed by appropriately selecting a nitrogen oxide-decomposing catalyst, for example, an Rh cermet, a material having a low catalytic activity, or a combination of a nitrogen oxide-decomposing catalyst arranged in the vicinity of a material having a low catalytic activity. In this embodiment, the detecting electrode 82 is composed of a porous cermet comprising Rh as a metal capable of reducing NOx as the objective gas component, and zirconia as a ceramic.

Accordingly, NOx existing in the measurement gas G introduced into the detecting electrode 82 through the protective layer 86 is decomposed by the catalytic action exerted by the detecting electrode 82. A constant voltage Vp2 at a level, at which $O_2$ produced from NOx decomposed by the detecting electrode 82 can be sufficiently pumped out toward the reference gas-introducing space 54, is applied between the detecting electrode 82 and the reference electrode 74 by the aid of a DC power source 88. NOx flows into the detecting electrode 82 while being limited by the protective layer 86. Under this condition, the DC power source 88 can apply a voltage having a magnitude sufficient to give a limiting current to the pumping for oxygen produced during the decomposition in the measuring pumping cell 84.

Thus a pumping current Ip2 is allowed to flow through the measuring pumping cell 84, corresponding to an amount of oxygen pumped out by the pumping operation performed by the measuring pumping cell 84. The pumping current Ip2 is detected by an ammeter 90.

A pumping voltage sufficient to decompose NOx may be applied between the detecting electrode 82 and the reference electrode 74. Alternatively, an oxide-decomposing catalyst for decomposing NOx may be arranged in the second chamber 62. Thus $O_2$ produced by the action of the pumping voltage and/or the oxide-decomposing catalyst may be pumped out from the second chamber 62 at a predetermined pumping voltage.

The oxide sensor 50A according to the first embodiment further comprises an electrochemical pumping cell, i.e., an auxiliary pumping cell 94 constructed by auxiliary pumping electrodes 92a to 92d (also referred to as the first auxiliary pumping electrodes) composed of porous cermet electrodes formed on inner wall surfaces of the second chamber 62, the reference electrode 74 (also referred to as the second auxiliary pumping electrode), the second solid electrolyte layer 52f, the second spacer layer 52e, and the first solid electrolyte layer 52d. The second auxiliary pumping electrode 74 is combined with the second detecting electrode 74 used with the first detecting electrode 82.

An auxiliary pumping voltage Vp3 is applied between the auxiliary pumping electrodes 92a to 92d and the reference electrode 74 of the auxiliary pumping cell 94 by the aid of a DC power source 96. Thus excessive $O_2$ introduced into the second chamber 62 can be pumped out to the outside of the second chamber 62.

Figure 3:
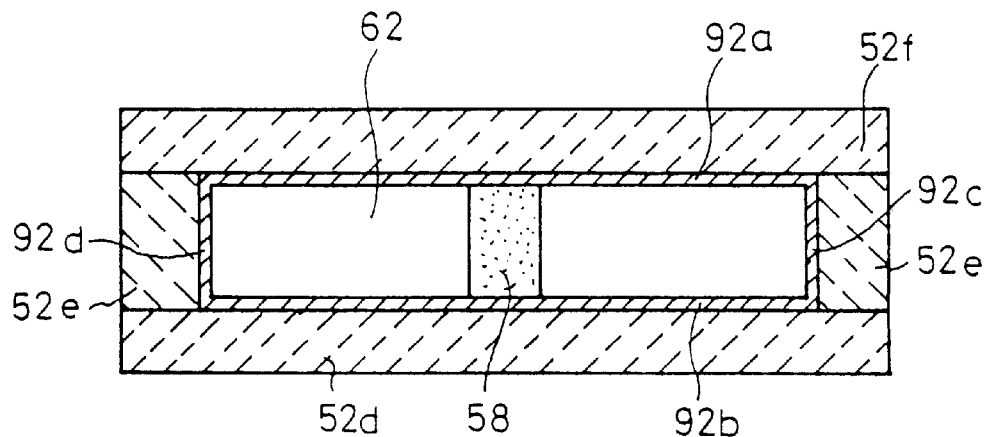
FIG. 3 shows a cross-sectional view taken along a line B—B in FIG. 2.
Figure 4:
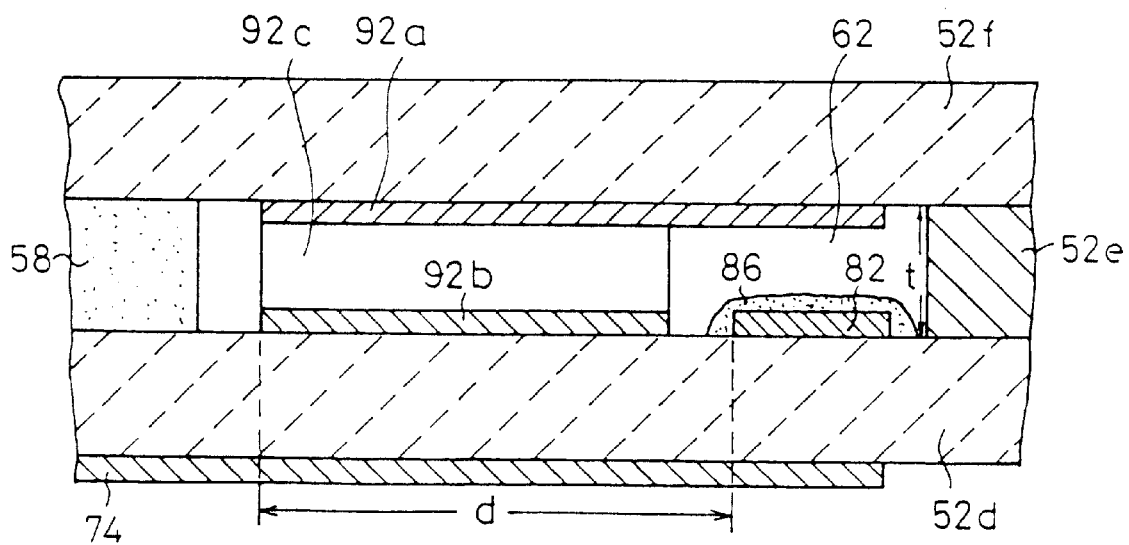
FIG. 4 shows an enlarged cross-sectional view illustrating a principal part of the oxide sensor according to the first embodiment.

As shown in FIGS. 3 and 4, the auxiliary pumping electrodes 92a to 92d are continuous to one another to surround the inner wall surfaces of the second chamber 62. The auxiliary pumping electrode 92a is arranged on the second solid electrolyte layer 52f which forms the upper surface of the wall surfaces for constructing the second chamber 62. The auxiliary pumping electrode 92b is arranged on the first solid electrolyte layer 52d which forms the lower surface of the wall surfaces for constructing the second chamber 62. The auxiliary pumping electrodes 92c, 92d are arranged on the spacer layer 52e which forms the side surfaces of the wall surfaces for constructing the second chamber 62. Thus the auxiliary pumping electrodes 92a, 92b, 92c, 92d are formed in a continuous manner.

The auxiliary pumping electrodes 92a to 92d are composed of a material having a weak reducing ability or no reducing ability with respect to NOx components in the measurement gas G in the same manner as the inner pumping electrode 64 of the main pumping cell 68. In this embodiment, the auxiliary pumping electrodes 92a to 92d are preferably composed of, for example, a compound having the perovskite structure such as $La_3CuO_4$, a cermet comprising a ceramic and a metal having a low catalytic activity such as Au, or a cermet comprising a ceramic, a metal of the Pt group, and a metal having a low catalytic activity such as Au. Further, when an alloy comprising Au and a metal of the Pt group is used as an electrode material, it is preferable to add Au in an amount of 0.03 to 35 vol % of the entire metal components.

Figure 5:
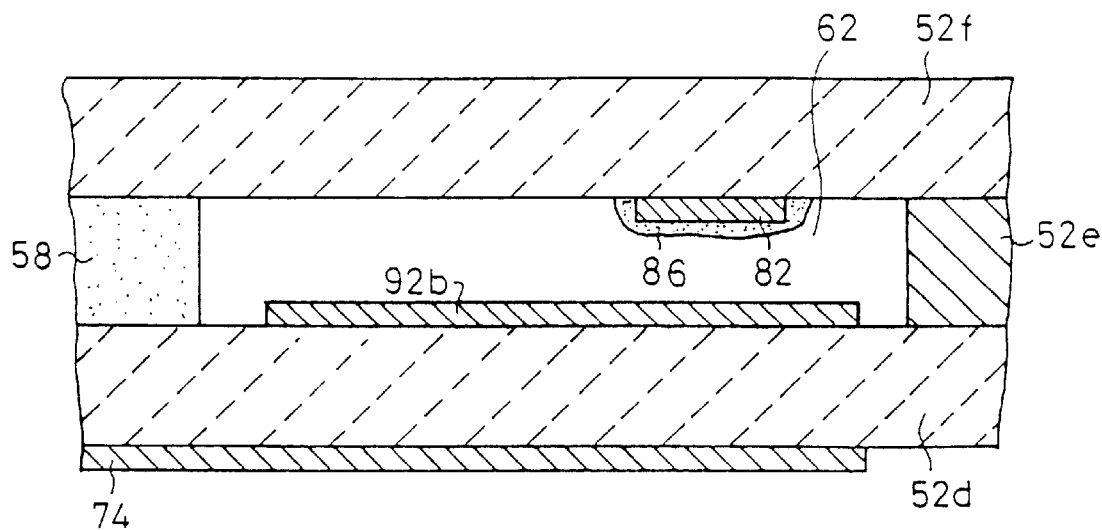
FIG. 5 shows another embodiment of the principal part of the oxide sensor according to the first embodiment.
Figure 6:
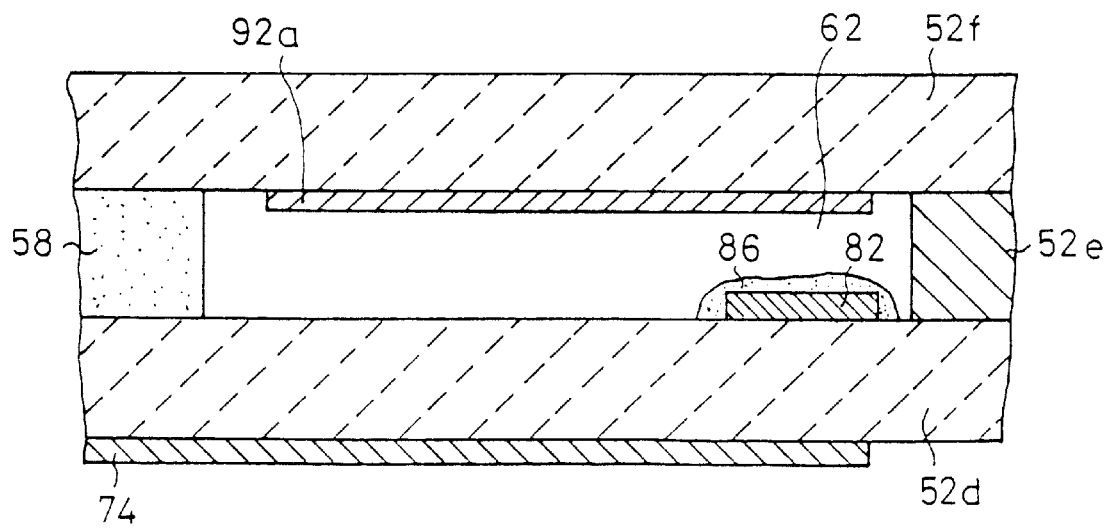
FIG. 6 shows still another embodiment of the principal part of the oxide sensor according to the first embodiment.

As shown in FIGS. 5 or 6, the auxiliary pumping electrodes 92a to 92d may be constructed as follows. Namely, it is allowable to provide only one electrode of any one of the auxiliary pumping electrode 92a arranged on the upper surface and the auxiliary pumping electrode 92b arranged on the lower surface. Alternatively, it is allowable to provide three electrodes of the auxiliary pumping electrodes 92a, 92b arranged on the both upper and lower surfaces and any one of the auxiliary pumping electrodes 92c, 92d arranged on the side surfaces.

In the present invention, as shown in FIG. 4, the detecting electrode 82 is arranged to satisfy the following expression:

$$d \geq t$$

provided that the distance d is measured from the upstream end of the auxiliary pumping electrodes 92a to 92d located on the side of the second diffusion rate-determining section 58 to the upstream end of the downstream positioned detecting electrode 82 as shown in FIG. 4, and the height of the second chamber 62 is t.

The detecting electrode 82 is set to have its area which is substantially ⅕ of an area of the auxiliary pumping electrodes 92a to 92d. It is preferable that the area of the detecting electrode 82 is not more than ⅕, or not more than ½ of the area of the auxiliary pumping electrodes 92a to 92d. The detecting electrode 82 is composed of an Rh cermet. The protective layer 86 for covering the surface of the detecting electrode 82 suppresses the reaction caused between inflammable gases contained in the measurement gas G and $O_2$ produced by the decomposition of oxides as the measurement-objective gas. Preferably, the protective layer 86 is composed of a porous material comprising a major component of alumina or zirconia.

As shown in FIG. 2, the oxide sensor 50A according to the first embodiment includes a heater 98 for generating heat in accordance with electric power supply from the outside. The heater 98 is embedded in a form of being vertically interposed between the first and second substrate layers 52a, 52b. The heater 98 is provided in order to increase the conductivity of oxygen ion. A ceramic layer 100 composed of alumina or the like is formed to cover upper and lower surfaces of the heater 98 so that the heater 98 is electrically insulated from the first and second substrate layers 52a, 52b.

The heater 98 is arranged to extend over an entire region ranging from the first chamber 60 to the second chamber 62. Thus the first and second chambers 60, 62 are heated to predetermined temperatures respectively. Further, the main pumping cell 68, the controlling oxygen partial pressure-detecting cell 76, the measuring pumping cell 84, and the auxiliary pumping cell 94 are also heated to and maintained at predetermined temperatures respectively.

The oxide sensor 50A according to the first embodiment is basically constructed as described above. Next, its function and effect will be explained.

Before the measurement of oxides, the oxide sensor 50A is set in a state in which the measurement gas G can be introduced into the first chamber 60. Next, an electric power is applied to the heater 98 so that the first and second solid electrolyte layers 52d, 52f are activated to have desired states.

Next, the measurement of oxides contained in the measurement gas G is started by introducing the measurement gas G into the oxide sensor 50A having been set as described above.

The measurement gas G is introduced into the first chamber 60 under a predetermined diffusion resistance through the first diffusion rate-determining section 56. The partial pressure of oxygen contained in the measurement gas G is controlled to have a predetermined value in accordance with a predetermined pumping voltage Vp1 applied between the inner pumping electrode 64 and the outer pumping electrode 66 by the aid of the variable power source 70.

Namely, the partial pressure of oxygen in the first chamber 60 can be measured on the basis of a voltage V1 between the reference electrode 74 and the measuring electrode 72, detected by the voltmeter 78. The voltage V1 is an electromotive force of the oxygen concentration cell defined by the Nernst's equation described above. The pumping voltage Vp1 applied by the variable power source 70 is controlled by the aid of the feedback control system 80 so that the voltage V1 is, for example, not more than 350 mV. Thus the partial pressure of oxygen in the first chamber 60 is controlled to have a predetermined value.

The measurement gas G, which has been controlled to have the predetermined partial pressure of oxygen in the first chamber 60, is introduced into the second chamber 62 through the second diffusion rate-determining section 58 designed to have a diffusion resistance larger than that of the first diffusion rate-determining section 56.

The auxiliary pumping electrodes 92a to 92d are arranged in the second chamber 62. Excessive $O_2$ contained in the introduced measurement gas is pumped out to the outside of the second chamber 62 in accordance with a predetermined auxiliary pumping voltage Vp3 applied between the auxiliary pumping electrodes 92a to 92d and the reference electrode 74 by the aid of the DC power source 96.

Oxides contained in the measurement gas G from which the excessive $O_2$ has been removed are decomposed by a predetermined measuring pumping voltage Vp2 applied by the DC power source 88 between the reference electrode 74 and the detecting electrode 82, or by the oxide-decomposing catalyst arranged in the second chamber 62. $O_2$ thus produced is pumped out toward the reference gas-introducing space 54 through the first solid electrolyte layer 52d. In this process, a current value Ip2, which is generated by movement of oxygen ion, is measured by the ammeter 90. The concentration of predetermined oxides, for example, NOx such as NO and $NO_2$ contained in the measurement gas G is determined from the current value Ip2.

Inflammable gases such as $H_2$ and CO are produced in the first chamber 60, due to the decomposition of $H_2O$ and $CO_2$ on the inner pumping electrode 64 as described above. The inflammable gases are introduced into the second chamber 62 together with the measurement gas G. In the present invention, the oxide sensor 50A according to the first embodiment is constructed as follows. Namely, the detecting electrode 82 for measuring the oxides, arranged in the second chamber 62 is located at the position separated from the second diffusion rate-determining section 58, farther than the position of the auxiliary pumping electrodes 92a to 92d. The area of the detecting electrode 82 is set to be not more than ½ of the area of the auxiliary pumping electrodes 92a to 92d. The surface of the detecting electrode 82 is covered with the protective layer 86. Accordingly, the reaction is suppressed between $O_2$ produced by the decomposition of the oxides on the detecting electrode 82 and the inflammable gases contained in the measurement gas G. Thus it is possible to measure the amount of the oxides with an extremely high degree of accuracy.

Now, experimental results will be described with reference to FIG. 7A and FIGS. 7B to 10.

Figure 7A:
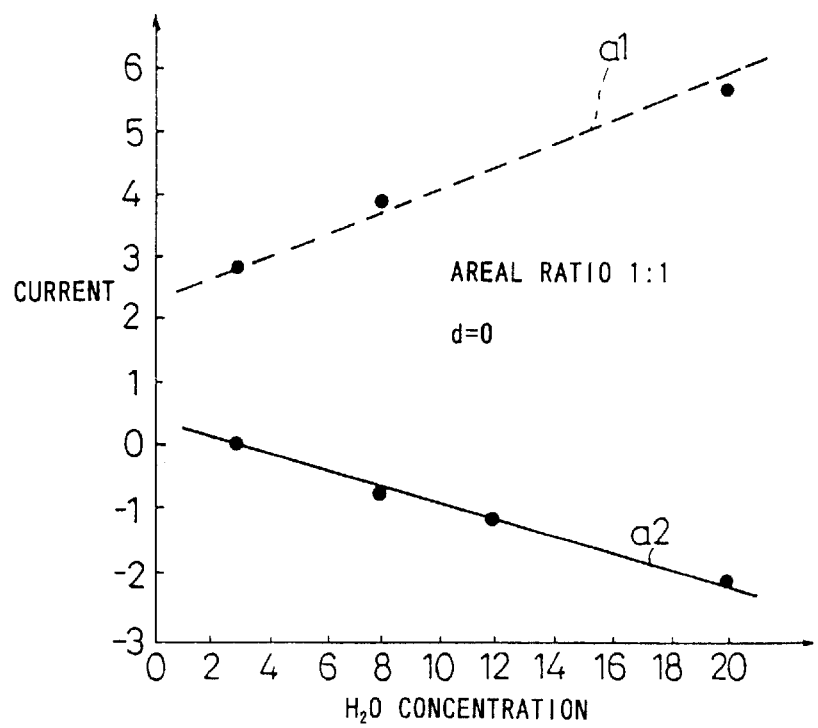
FIG. 7A shows characteristics representing the relationship among the value of current flowing through an auxiliary pumping electrode, the value of current flowing through a detecting electrode, and the concentration of $H_2O$, concerning Comparative Example.

FIG. 7A shows experimental results obtained in Comparative Example by using an oxide sensor constructed as follows. Namely, only the auxiliary pumping electrode 92a was provided. The areal ratio of the auxiliary pumping electrode 92a to the detecting electrode 82 was set to be 1:1. The distance of the auxiliary pumping electrode 92a from the second diffusion rate-determining section 58 was the same as that of the detecting electrode 82 (d=0). The protective layer 86 was not provided for the detecting electrode 82. Under this condition, measurement was made for the current a1 flowing between the auxiliary pumping electrode 92a and the reference electrode 74 and the current a2 flowing between the detecting electrode 82 and the reference electrode 74 after introducing a measurement gas G containing $H_2O$ and NO.

In Comparative Example, the current a2 representing the concentration of NO was decreased, while the current a1 flowing through the auxiliary pumping electrode 92 was increased, as the concentration of $H_2O$ in the measurement gas G was increased.

Figure 7B:
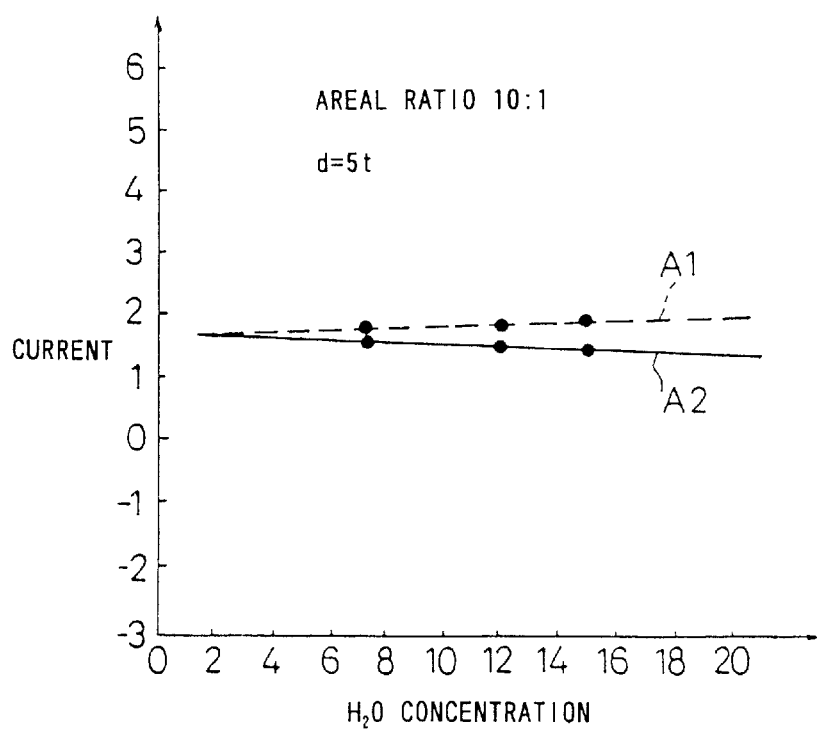
FIG. 7B shows characteristics representing the relationship among the value of current flowing through auxiliary pumping electrodes, the value of current flowing through a detecting electrode, and the concentration of $H_2O$, concerning Example 1.

FIG. 7B shows results obtained in Example 1 constructed in the same manner as the oxide sensor 50A according to the first embodiment shown in FIG. 4. In Example 1, the areal ratio of the auxiliary pumping electrodes 92a to 92d to the detecting electrode 82 was set to be 10:1. The detecting electrode 82 was separated by the distance d (d=5t, see FIG. 4) from the second diffusion rate-determining section 58, farther than the auxiliary pumping electrodes 92a to 92d. The protective layer 86 was provided for the detecting electrode 82. Under this condition, measurement was made for the current A1 flowing between the auxiliary pumping electrodes 92a to 92d and the reference electrode 74 and the current A2 flowing between the detecting electrode 82 and the reference electrode 74 after introducing the same measurement gas G as that used in FIG. 7A.

In Example 1, the currents A1 and A2 were substantially constant, regardless of the concentration of $H_2O$ in the measurement gas G.

FIG. 8 shows results obtained in Example 2 constructed in the same manner as the oxide sensor 50A according to the first embodiment shown in FIG. 6. In Example 2, the areal ratio of the auxiliary pumping electrodes 92a to 92d to the detecting electrode 82 was set to be 5:1. The detecting electrode 82 was separated by the distance d (d=2t, see FIG. 4) from the second diffusion rate-determining section 58, farther than the auxiliary pumping electrodes 92a to 92d. The protective layer 86 was provided for the detecting electrode 82. Under this condition, measurement was made for the current B1 flowing between the auxiliary pumping electrodes 92a to 92d and the reference electrode 74 and the current B2 flowing between the detecting electrode 82 and the reference electrode 74 after introducing the same measurement gas G as that used in FIGS. 7A and 7B.

The results were also obtained in Example 2 as follows. Namely, the fluctuation of the currents B1 and B2 was extremely minimized, regardless of the concentration of $H_2O$ in the measurement gas G.

FIG. 9 shows results obtained in Example 3 constructed in the same manner as the oxide sensor 50A according to the first embodiment shown in FIG. 6. In Example 3, the areal ratio of the auxiliary pumping electrodes 92a to 92d to the detecting electrode 82 was fixed to be 2:1. Under this condition, measurement was performed by changing the separating distance d between the upstream end of the auxiliary pumping electrodes 92a to 92d and the upstream end of the detecting electrode 82. In Example 3, the fluctuation of oxygen concentration was considerably decreased in a range of $d \geq t$.

FIG. 10 shows results obtained in Example 4 constructed in the same manner as the oxide sensor 50A according to the first embodiment shown in FIG. 6. In Example 4, the separating distance d between the end of the auxiliary pumping electrodes 92a to 92d and the end of the detecting electrode 82 was fixed to be d=t. Under this condition, measurement was performed by changing the areal ratio of the auxiliary pumping electrodes 92a to 92d to the detecting electrode 82.

In Example 4, the fluctuation of oxygen concentration was considerably decreased in a range in which the areal ratio was not less than 2:1.

According to the results described above, the following facts have been demonstrated. In Comparative Example shown in FIG. 7A, the detecting electrode 82 and the auxiliary pumping electrode 92a are separated by the same distance (d=0) from the second diffusion rate-determining section 58, or the areal ratio of the detecting electrode 82 to the auxiliary pumping electrode 92a is 1:1. In Comparative Example constructed as described above, for example, it is assumed that a part of $H_2O$ contained in the measurement gas G introduced into the first chamber 60 is decomposed by the inner pumping electrode 64 to produce $H_2$. The produced $H_2$ is introduced into the second chamber 62 together with NO as the measurement-objective gas, and the $H_2$ reacts with $O_2$ produced by decomposition of NO on the detecting electrode 82 to form $H_2O$ again.

During this process, the oxygen concentration is lowered in the vicinity of the detecting electrode 82. Accordingly, $O_2$ is pumped into the second chamber 62 from the outside in a reverse manner through the first and second solid electrolyte layers 52d, 52f. As a result, the current a2 is decreased. On the other hand, the current a1 flowing through the auxiliary pumping electrode 92a is increased to pump out the $O_2$ having been pumped into the second chamber 62. Therefore, the current a2, which represents the concentration of NO, fluctuates depending on the concentration of $H_2O$ contained in the measurement gas G. Consequently, it is impossible to highly accurately detect the concentration of NO.

On the contrary, in Example 1 shown in FIG. 7B, the detecting electrode 82 is separated from the second diffusion rate-determining section 58, farther than the auxiliary pumping electrodes 92a to 92d by not less than a predetermined distance, preferably by not less than the distance d to satisfy $d \geq t$. Thus a state is established, in which $H_2$ scarcely arrives at the detecting electrode 82. Further, the arrival of $H_2$ at the detecting electrode 82 itself is appropriately suppressed by covering the surface of the detecting electrode 82 with the protective layer 86. Moreover, the reaction between $H_2O$ and $O_2$ scarcely occurs in the vicinity of the detecting electrode 82 by setting the area of the detecting electrode 82 to be smaller than the area of the auxiliary pumping electrodes 92a to 92d, preferably by setting the area of the detecting electrode 82 to be not more than ½ of the area of the auxiliary pumping electrodes 92a to 92d.

Because of the reasons described above, $H_2$ scarcely reacts with $O_2$ produced from NO. As a result, the amount of NO contained in the measurement gas G can be highly accurately detected from a value of the current flowing through the detecting electrode 82, regardless of the concentration of $H_2O$. In the same manner as described above, the concentration of oxides such as NO and $NO_2$ can be highly accurately measured without being affected by the inflammable gas produced from $CO_2$.

The oxide sensor 50A according to the first embodiment has been explained in a form in which only one second chamber 62 is linked to the first chamber 60. However, it is also allowable to provide a plurality of the second chambers 62 connected to the first chamber 60 so that a plurality of oxides of different types may be simultaneously measured.

For example, a third chamber constructed in the same manner as the second chamber 62 is provided and connected in series to the second chamber 62 through a diffusion rate-determining section. Further, a pumping voltage, which is different from the pumping voltage Vp2 applied to the detecting electrode 82 for the second chamber 62, is applied to an electrode for the third chamber. Thus it is possible to measure oxides of a type different from those measured in the second chamber 62. The oxides include, for example, NO, $NO_2$, $CO_2$, $H_2O$, and $SO_2$. It is also possible to connect the third chamber to the second chamber 62 in parallel.

Next, an oxide sensor 50B according to a second embodiment will be explained with reference to FIG. 11. Components or parts of the oxide sensor 50B corresponding to those shown in FIG. 2 are designated by the same reference numerals, duplicate explanation of which will be omitted.

Figure 11:
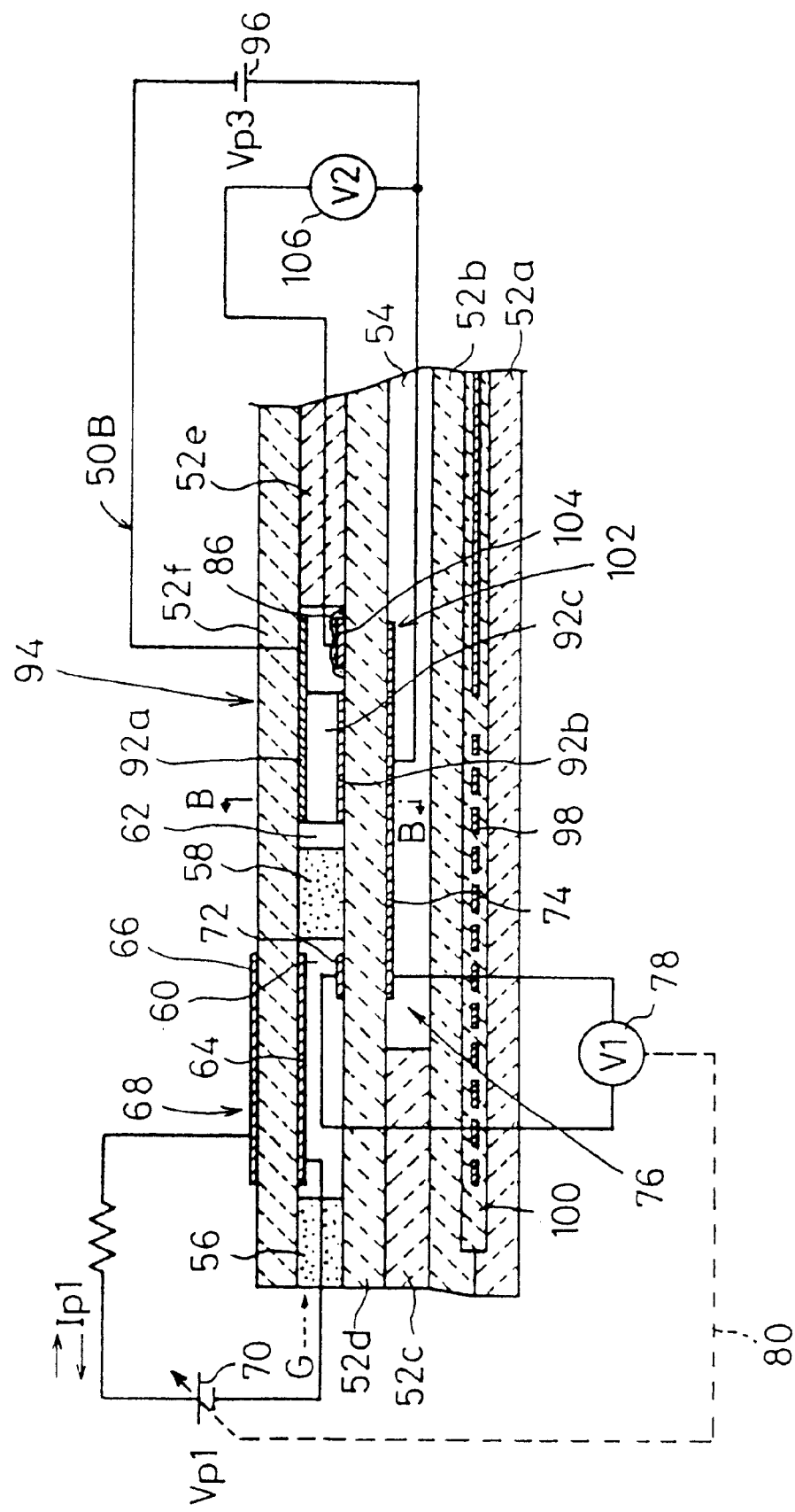
FIG. 11 shows a cross-sectional view illustrating an oxide sensor according to a second embodiment.

As shown in FIG. 11, the oxide sensor 50B according to the second embodiment has approximately the same structure as that of the oxide sensor 50A according to the first embodiment (see FIG. 2). However, the former is different from the latter in that a measuring oxygen partial pressure-detecting cell 102 is provided in place of the measuring pumping cell 84.

The measuring oxygen partial pressure-detecting cell 102 comprises a detecting electrode 104 formed on a portion for forming the second chamber 62, of the upper surface of the first solid electrolyte layer 52d, the reference electrode 74 formed on the lower surface of the first solid electrolyte layer 52d, and the first solid electrolyte layer 52d.

In this embodiment, an electromotive force (electromotive force of an oxygen concentration cell) V2 is generated between the detecting electrode 104 and the reference electrode 74 of the measuring oxygen partial pressure-detecting cell 102, corresponding to a difference in oxygen concentration between an atmosphere around the detecting electrode 104 and an atmosphere around the reference electrode 74.

Therefore, the partial pressure of oxygen in the atmosphere around the detecting electrode 104, in other words, the partial pressure of oxygen defined by oxygen produced by reduction or decomposition of the measurement gas components (NOx) is detected as a value of the voltage V2 by measuring the electromotive force (voltage) V2 generated between the detecting electrode 104 and the reference electrode 74 by using a voltmeter 106.

The degree of change in electromotive force V2 represents the NOx concentration. Namely, the electromotive force V2, which is outputted from the measuring oxygen partial pressure-detecting cell 102 constructed by the detecting electrode 104, the reference electrode 74, and the first solid electrolyte layer 52d, represents the NOx concentration in the measurement gas G.

Therefore, in the oxide sensor 50B according to the second embodiment constructed as described above, the measurement gas G, which has been controlled for its partial pressure of oxygen in the second chamber 62, is also introduced into the detecting electrode 104 under a predetermined diffusion resistance through the protective layer 84.

In this embodiment, the partial pressure of oxygen in the atmosphere in the second chamber 62 is in a situation in which the measurement gas components (NOx) are not substantially reduced or decomposed, while giving a low value of the partial pressure of oxygen at which the measurement of the amount of the objective components is not substantially affected, in the same manner as the oxide sensor 50A according to the first embodiment. The change in amount of oxygen introduced into the second chamber 62 is greatly reduced as compared with the change which occurs in the measurement gas G, owing to the operation of the main pumping cell 68 in the first chamber 60. Therefore, the partial pressure of oxygen in the second chamber 62 is controlled accurately and constantly.

Therefore, even when the oxygen concentration in the measurement gas G greatly changes, it is possible to accurately measure the NOx concentration, based on the use of the measuring oxygen partial pressure-detecting cell 102 by the aid of the voltmeter 106.

Figure 12:
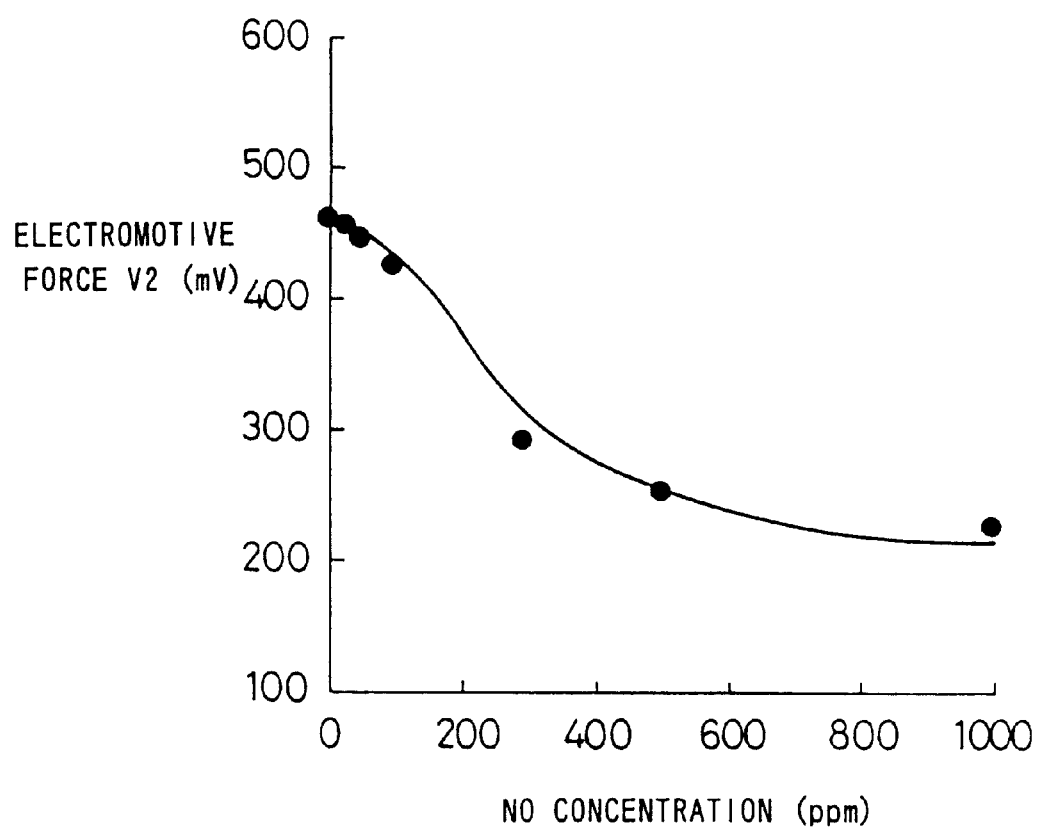
FIG. 12 shows a characteristic of the oxide sensor according to the second embodiment, illustrating the change in electromotive force generated in a measuring oxygen partial pressure-detecting cell depending on the change in NO concentration.

Now, the principle of detection performed by the oxide sensor 50B according to the second embodiment will be explained with reference to FIG. 12 illustrating a characteristic of the oxide sensor 50B.

At first, when the NO concentration in the external space is 0 ppm, the pumping voltage Vp1 of the main pumping cell 68 is controlled so that the partial pressure of oxygen in the atmosphere in the first chamber 60 is maintained to be $1.3 \times 10^{-7}$ atm, i.e., to give a value of the electromotive force V1=about 300 mV.

Next, the set voltage Vp3 applied to the auxiliary pumping cell 94 is set to be 460 mV. The partial pressure of oxygen in the second chamber 62 is controlled to be $6.1 \times 10^{-11}$ atm owing to the operation performed by the auxiliary pumping cell 94. As a result, the electromotive force V2 between the detecting electrode 104 and the reference electrode 74 of the measuring oxygen partial pressure-detecting cell 102 is about 460 mV.

In this case, the inflammable gas components are oxidized in the first chamber 60, and the sensitivity to NOx is not affected thereby, because the partial pressure of oxygen in the first chamber 60 is $1.3 \times 10^{-7}$ atm, regardless of the fact that the partial pressure of oxygen in the second chamber 62 is $6.1 \times 10^{-11}$ atm.

If the NO concentration in the external space gradually increases, the reduction or decomposition reaction of NO is caused on the detecting electrode 104, because the detecting electrode 104 also functions as a NOx-reducing catalyst in the same manner as the detecting electrode 82 of the measuring pumping cell 84 described above (see FIG. 2). As a result, the oxygen concentration in the atmosphere around the detecting electrode 104 is increased. Accordingly, the electromotive force V2 generated between the detecting electrode 104 and the reference electrode 74 is gradually decreased. With reference to FIG. 12 illustrating the characteristic of the oxide sensor 50B, for example, when the NO concentration increases to 300 ppm, 500 ppm, and 1000 ppm, the electromotive force V2 detected by the voltmeter 106 is gradually decreased to 300 mV, 250 mV, and 220 mV respectively.

The degree of the decrease in electromotive force V2 represents the NO concentration. Namely, the electromotive force V2, which is outputted from the measuring oxygen partial pressure-detecting cell 102 constructed by the detecting electrode 104, the reference electrode 74, and the first solid electrolyte layer 52d, represents the NO concentration in the measurement gas G.

Next, an illustrative experiment will be described. The illustrative experiment was performed by providing Example and Comparative Example, in which observation was made for the change in electromotive force V2 generated in the measuring oxygen partial pressure-detecting cell 102, by changing the $H_2O$ concentration in a range of 0 to 25% in a measurement gas G comprising basic gas components of an NO—$O_2$—$H_2O$—$N_2$ system.

In the illustrative experiment, Example was based on the use of a system constructed in the same manner as the oxide sensor 50B according to the second embodiment, in which the areal ratio of the auxiliary pumping electrodes 92a to 92d to the detecting electrode 104 was set to be 10:1, the detecting electrode 104 was separated from the second diffusion rate-determining section 58, farther than the auxiliary pumping electrodes 92a to 92d by the distance d (d=5t, see FIG. 4), and the protective layer was provided for the detecting electrode 104.

On the other hand, Comparative Example was based on the use of a system concerning the oxide sensor according to the second embodiment, in which only the auxiliary pumping electrode 92a was provided, the areal ratio of the auxiliary pumping electrode 92a to the detecting electrode 104 was set to be 1:1, the auxiliary pumping electrode 92a and the detecting electrode 104 were separated from the second diffusion rate-determining section 58 by the same distance d (d=0), and the protective layer was not provided for the detecting electrode 104.

In the illustrative experiment, the pumping voltage Vp1 (equivalent to the electromotive force V1) of the main pumping cell 68 was 300 mV, and the auxiliary pumping voltage Vp3 of the auxiliary pumping cell 94 was 460 mV.

Figure 13:
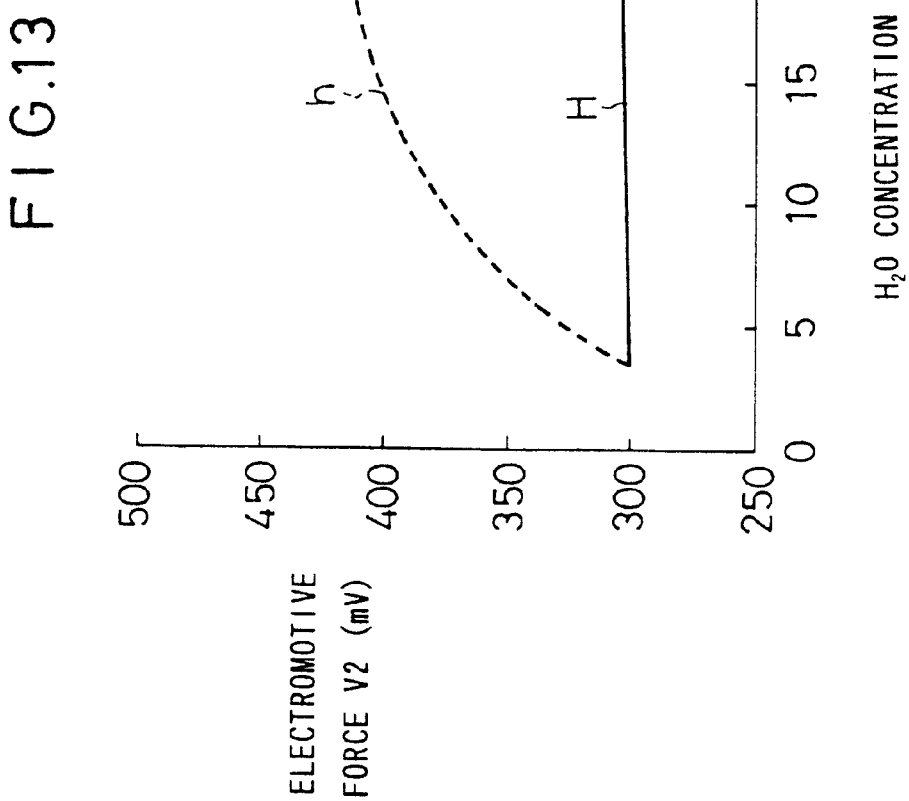
FIG. 13 shows an illustrative experiment obtained by using the oxide sensor according to the second embodiment, illustrating characteristics representing the relationship between the $H_2O$ concentration in a measurement gas and the electromotive force V2 generated in a measuring oxygen partial pressure-detecting cell.
Figure 14:
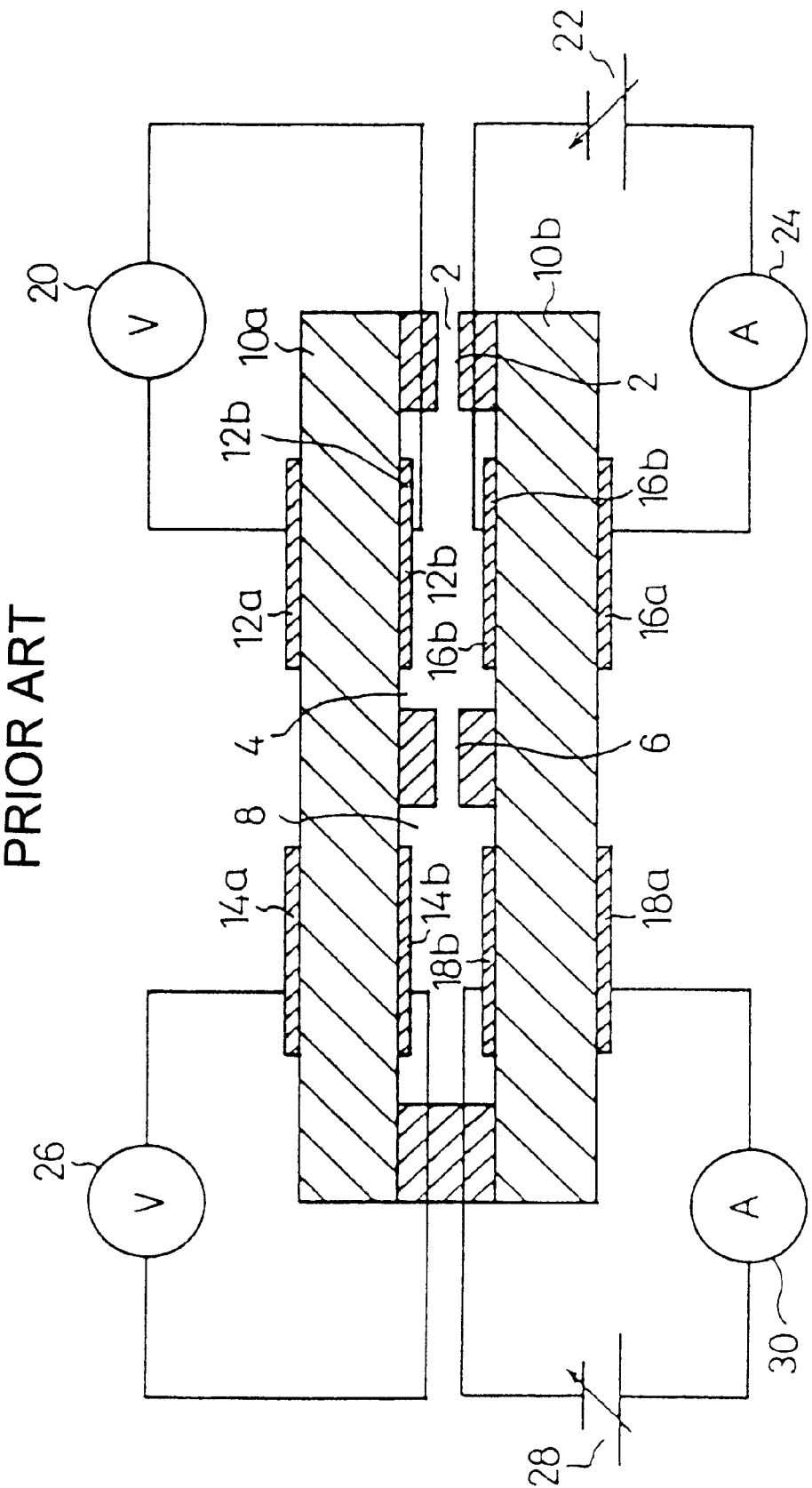
FIG. 14 shows a cross-sectional view illustrating a system of a gas analyzer concerning the conventional technique.

Experimental results obtained in the illustrative experiment are shown in FIG. 13. In FIG. 13, a characteristic curve H indicated by a solid line represents an experimental result obtained in Example, and a characteristic curve h indicated by a broken line represents an experimental result obtained in Comparative Example.

As clarified from the experimental results shown in FIG. 13, the electromotive force V2 increases in Comparative Example, as the $H_2O$ concentration in the measurement gas G becomes high. For example, when the $H_2O$ concentration is 0%, the electromotive force is 300 mV. However, when the $H_2O$ concentration is 25%, the electromotive force is about 420 mV.

On the contrary, in Example, the areal ratio of the auxiliary pumping electrodes 92a to 92d to the detecting electrode 104 of the auxiliary pumping cell 94 is 10:1, the detecting electrode 104 is separated from the second diffusion rate-determining section 58, farther than the auxiliary pumping electrodes 92a to 92d by the distance d=5t, and the protective layer 86 is provided for the detecting electrode 104. Accordingly, it is understood that even when the $H_2O$ concentration in the measurement gas G changes in a range of 0 to 25%, the electromotive force V2 generated in the measuring oxygen partial pressure-detecting cell 102 scarcely changes, and thus the dependency of the electromotive force V2 on $H_2O$ is extremely minimized.

Accordingly, when the measurement gas G contains the NO component, the electromotive force V2 corresponding to an amount of NO is generated between the detecting electrode 104 and the reference electrode 74 for constructing the measuring oxygen partial pressure-detecting cell 102. The amount of NO can be correctly determined by detecting the electromotive force V2.

As described above, the detecting electrode 104 for measuring the oxides, arranged in the second chamber 62 is located at the position separated from the second diffusion rate-determining section 58, farther than the position of the auxiliary pumping electrodes 92a to 92d, the area of the detecting electrode 104 is set to be not more than ½ of the area of the auxiliary pumping electrodes 92a to 92d, and the surface of the detecting electrode 104 is covered with the protective layer 86, also in the oxide sensor 50B according to the second embodiment, in the same manner as the oxide sensor 50A according to the first embodiment. Accordingly, the reaction is suppressed between the $O_2$ produced by the decomposition of oxides on the detecting electrode 104 and the inflammable gases contained in the measurement gas G. Thus the amount of the oxides can be measured with an extremely high degree of accuracy.

It is a matter of course that the oxide sensor according to this invention is not limited to the embodiments described above, which can be constructed in other various forms without deviating from the gist or essential characteristics of this invention.

What is claimed is:

1. An oxide sensor comprising:

a main pumping means including inner and outer pumping electrodes arranged respectively on an inside surface and an outside surface of a first process space formed in a substrate composed of an oxygen ion-conductive solid electrolyte, for performing a pumping process for oxygen contained in a measurement gas introduced from an external space into said first process space, on the basis of a control voltage applied between said inner and outer pumping electrodes, said inner pumping electrode being arranged inside said first process space;

an electric signal-generating conversion means including first and second detecting electrodes which are arranged on an inside surface and an outside surface of a second process space formed in said substrate, for decomposing oxides contained in said measurement gas in said second process space after being subjected to said pumping process performed by said main pumping means, by the aid of a catalytic action and/or electrolysis to provide, by conversion, an electric signal corresponding to an amount of oxygen produced by said decomposition, said first and second process spaces being defined separated from each other inside said substrate, wherein said first process space communicates with said second process space through a diffusion rate-determining section; and an auxiliary pumping means including first and second auxiliary pumping electrodes which are arranged on the inside surface and the outside surface of said second process space formed in said substrate, for performing a pumping process for oxygen contained in said measurement gas in said second process space after being subjected to said pumping process performed by said main pumping means, on the basis of an auxiliary pumping voltage applied between said first and second auxiliary pumping electrodes, said first auxiliary pumping electrode being arranged inside said second process space, wherein:

said first detecting electrode is arranged in said second process space at a position having an upstream end of said detecting electrode separated from the upstream end of said first auxiliary pumping electrode, said position of the upstream end of the detecting electrode being on a downstream side of a flow of said measurement gas from the upstream end of said first auxiliary pumping electrode; and said oxides contained in said measurement gas are measured on the basis of said electric signal supplied from said electric signal-generating conversion means.

2. The oxide sensor according to claim 1, wherein said electric signal-generating conversion means comprises:

a measuring pumping means including said first and second detecting electrodes, for decomposing said oxides contained in said measurement gas after being subjected to said pumping process performed by said main pumping means, by the aid of said catalytic action and/or electrolysis, and performing a pumping process for said oxygen produced by said decomposition on the basis of a measuring voltage applied between said first and second detecting electrodes; and a current-detecting means for detecting a pumping current generated corresponding to an amount of said oxygen subjected to said pumping process performed by said measuring pumping means, wherein:

said oxides in said measurement gas are measured on the basis of said pumping current detected by said current-detecting means.

3. The oxide sensor according to claim 1, wherein said electric signal-generating conversion means comprises:

a concentration-detecting means including said first and second detecting electrodes, for decomposing said oxides contained in said measurement gas after being subjected to said pumping process performed by said main pumping means, by the aid of said catalytic action, and generating an electromotive force corresponding to a difference between said amount of oxygen produced by said decomposition and an amount of oxygen contained in a gas existing on a side of said second detecting electrode; and a voltage-detecting means for detecting said electromotive force generated by said concentration-detecting means, wherein:

said oxides in said measurement gas are measured on the basis of said electromotive force detected by said voltage-detecting means.

4. The oxide sensor according to claim 1, wherein the upstream end of said first detecting electrode is arranged at a position separated by a distance d from the upstream end of said first auxiliary pumping electrode, wherein d is greater than or equal to t and t represents a height of said second process space for said measurement gas after being subjected to said pumping process performed by said main pumping means.

5. The oxide sensor according to claim 1, wherein said first detecting electrode has an area which is set to be not more than ½ of an area of said first auxiliary pumping electrodes.

6. The oxide sensor according to claim 1, wherein said first detecting electrode has an area which is set to be not more than ⅕ of an area of said first auxiliary pumping electrodes.

7. The oxide sensor according to claim 1, wherein said first detecting electrode is covered with a protective layer composed of a porous material.

8. The oxide sensor according to claim 1, wherein said first auxiliary pumping electrode have portions arranged on at least upper and lower surfaces of said second process space for said measurement gas after being subjected to said pumping process performed by said main pumping means, and said first auxiliary pumping electrode portions are connected to one another.

9. The oxide sensor according to claim 1, wherein said first auxiliary pumping electrode is composed of an inactive material having a low catalytic activity on said oxides.

10. The oxide sensor according to claim 1, wherein said inner pumping electrode is composed of an inactive material having a low catalytic activity on said oxides.

11. The oxide sensor according to claim 1, wherein said second detecting electrode is arranged at a position exposed to a space into which a reference gas is introduced.

12. The oxide sensor according to claim 1, wherein said second detecting electrode is combined into a common unit with said second auxiliary pumping electrode.

* * * * *